(12) United States Patent
Edirisuriya et al.

(10) Patent No.: US 7,157,035 B2
(45) Date of Patent: *Jan. 2, 2007

(54) METHOD OF FORMING A RESPIRATORY CONDUIT

(75) Inventors: Deshitha Airawana Edirisuriya, Auckland (NZ); David Peter Baldwin, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 598 days.

This patent is subject to a terminal disclaimer.

(21) Appl. No.: 10/314,812

(22) Filed: Dec. 9, 2002

(65) Prior Publication Data

US 2003/0111249 A1 Jun. 19, 2003

(30) Foreign Application Priority Data

Dec. 14, 2001 (NZ) .................................. 516153

(51) Int. Cl.
*B29C 45/14* (2006.01)

(52) U.S. Cl. .................... 264/263; 264/271.1; 264/320

(58) Field of Classification Search ..................... None
See application file for complete search history.

(56) References Cited

U.S. PATENT DOCUMENTS

| | | | | |
|---|---|---|---|---|
| 2,561,351 A | * | 7/1951 | Fentress | ................ 285/148.13 |
| 3,287,485 A | * | 11/1966 | McCord | ..................... 264/263 |
| 3,963,856 A | * | 6/1976 | Carlson et al. | ................ 174/47 |
| 4,235,832 A | * | 11/1980 | Leighton | ..................... 264/230 |
| 4,292,267 A | * | 9/1981 | Haynes | ........................ 264/157 |
| 4,348,348 A | * | 9/1982 | Bennett et al. | .............. 264/255 |
| 4,490,575 A | * | 12/1984 | Kutnyak | ....................... 174/47 |
| 5,234,515 A | * | 8/1993 | Sekkelsten | .................... 156/49 |
| 5,302,336 A | * | 4/1994 | Hartel et al. | ................. 264/263 |
| 5,848,223 A | | 12/1998 | Carlson | |
| 6,123,111 A | * | 9/2000 | Nathan et al. | .............. 138/109 |
| 6,190,480 B1 | * | 2/2001 | Carlson | ...................... 156/143 |
| 6,219,490 B1 | * | 4/2001 | Gibertoni et al. | ........... 392/472 |

FOREIGN PATENT DOCUMENTS

| | | |
|---|---|---|
| DE | 19800986 | 7/1999 |
| FR | 717210 | 1/1932 |
| FR | 2717556 | 9/1995 |

* cited by examiner

*Primary Examiner*—Edmund H. Lee
(74) *Attorney, Agent, or Firm*—Trexler, Bushnell, Giangiorgi, Blackstone & Marr, Ltd

(57) ABSTRACT

The present invention relates to delivery conduits used in systems that provide positive pressure ventilation therapy. In particular, the present invention relates to a sleeve that allows flexible conduits to be joined and sealed to a thermoplastic connector, allowing for gases to be supplied to the conduit. The sleeve is used in the over moulding of an end connector onto the conduit. The sleeve and method of attaching a connector to a conduit of the present invention has the advantage that it prevents the connector from loosening or breaking when the conduit is bent, pulled or stressed, which can occur in some cases where the connector is attached to the conduit using a bond, such as glue. Furthermore, the occurrences of flashing of plastic across the conduit walls will be prevented during moulding, ensuring that no air or water leakages occur within the conduit walls.

3 Claims, 3 Drawing Sheets

METHOD OF FORMING A RESPIRATORY CONDUIT

BACKGROUND OF THE INVENTION

1. Field of the Invention

The present invention relates to delivery conduits used in systems that provide positive pressure ventilation therapy. In particular, the present invention relates to a method of forming a connector on a conduit and a sleeve used in the method that allows flexible conduits to be joined and sealed to a thermoplastic connector, allowing for gases to be supplied to the conduit.

2. Summary of the Prior Art

Administration of positive pressure ventilation is a common method of treating Obstructive Sleep Apnoea syndrome and Upper Airway Resistance syndrome. Some forms of delivery systems that can be used for ventilation therapy are; CPAP (Continuous Positive Airway Pressure), VPAP (Variable Positive Airway Pressure) and BiPAP (Bi-level Positive Airway Pressure).

The delivery of gases to the patient requires, in the very least, a nose, mouth, or face mask fitted to the patient with a connection via a flexible gases delivery conduit to a gases flow generator. One requirement of the delivery conduit is to provide humidified air at a particular pressure to the patient, via the mask. The conduit therefore requires connectors at each end that provide effective sealing and connection of the conduit to the mask, humidifier and/or air flow generator of the positive pressure ventilation system, so that there is no or low pressure loss along the delivery conduit.

There are a variety of methods for fitting a connector to a flexible helically wound conduit, such as the tubing disclosed in U.S. Pat. No. 584,223. This patent discloses a conduit that is a tube having a helically wound support bead between inner and outer walls. A helically wrapped electrical resistance heating conduit is disposed adjacent to the inner wall, in good heat transfer relation to fluid and/or air that flows within the tube. The majority of these connections are made by threading the connector onto the conduit and then gluing the connector to the conduit. For example, U.S. Pat. No. 3,963,856 discloses a connection or fitting that is bonded to a conduit or tubing. The fitting has an internal thread that is simply threaded onto the external bead or wall of the tubing. Here it is disclosed that the bond may be adhesive or of the heat seal type. A further other commonly used method is to mould the connector directly onto the conduit.

The abovementioned methods are operator intensive and/or may result in the conduit being damaged. Usage and bending of the flexible conduit may cause loss of adherence from the glue and it may also cause breakages where the conduit is stressed during the moulding process.

A further method used is the over moulding of the connector onto a clip and conduit, where the clip is attached to one end of the conduit. Here the clip is partially annular in shape and is placed over and in between a cut made in the outer wall of the conduit, therefore the clip sits in between the bead. A connector is then moulded around the clip and conduit. With this method the conduit is often compressed, and with high temperatures and pressures used during moulding excess plastic flashing can be forced from the mould across the connector to the outer wall of the tubing.

Plastic flashings and hot plastic, may during moulding touch the outer wall of the conduit at the connector interface causing damage to the tubing walls, leading to water and air seepage into and out of the conduit.

SUMMARY OF THE INVENTION

It is an object of the present invention to provide a method of forming a ventilation conduit that goes some way to overcoming the abovementioned disadvantages in the prior art or which will at least provide the industry with a useful choice.

Accordingly in a first aspect the present invention may broadly be said to consist in a method of forming a connector on one end of a length of flexible conduit, using an intermediary sleeve to protect said conduit, said sleeve comprising:

a section of hollow cylinder and having a thread on its interior surface, of corresponding size and shape to the outer surface of said conduit, so that said cylinder can be threaded onto said at least one free end, wherein said method comprises the steps of:

a) threading said sleeve onto said at least one free end, b) moulding said connector over said conduit and said sleeve, said moulding causing said sleeve to become an integral part of the inner surface of said connector.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

BRIEF DESCRIPTION OF THE DRAWINGS

One preferred form of the present invention will now be described with reference to the accompanying drawings in which.

DETAILED DESCRIPTION OF THE PREFERRED EMBODIMENTS

The preferred embodiment of the sleeve of the present invention is used in the over moulding of an end connector onto a delivery conduit that may be used in medical apparatus or ventilation therapy systems. The connector allows for the delivery conduit to be connected to other apparatus in the ventilation system, such as, an air generator, humidifier or mask. In particular, the delivery conduit must be capable of providing air, usually humidified, to the patient at a particular pressure, in order for ventilation therapy to be successful.

Figure 1:
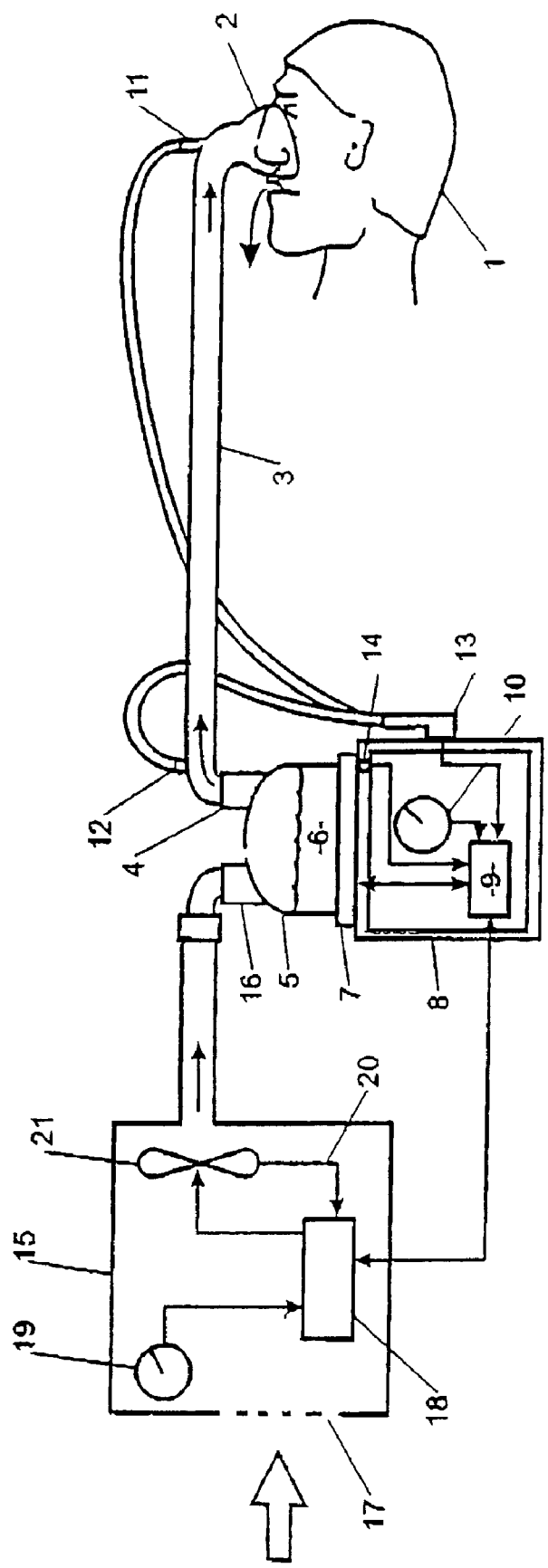
FIG. 1 is a schematic view of ventilation apparatus that may utilise the conduit formed from the method of the present invention.

A typical patient ventilation therapy system that uses such a flexible delivery conduit of the type associated with the present invention is shown in FIG. 1. Here, a humidified positive pressure ventilation system is shown in which a patient 1 is receiving humidified and pressurised gases through a patient interface 2 connected to a humidified gases transportation pathway or delivery conduit 3. Delivery conduit 3 is connected to the outlet 4 of a humidification chamber 5, which contains a volume of water 6. Delivery conduit 3 usually contains heating means or heater wires (not shown), which heat the walls of the conduit to reduce condensation of humidified gases within the conduit. Humidification chamber 6 is preferably formed from a plastics material and may have a highly heat conductive base (for example an aluminium base) which is in direct contact with a heater plate 7 of humidifier 8. Humidifier 8 is provided with control means or electronic controller 9 which may comprise a microprocessor based controller executing computer software commands stored in associated memory.

Controller 9 receives input from sources such as user input means or dial 10 through which a user of the device may, for example, set a predetermined required value (preset value) of humidity or temperature of the gases supplied to patient 1. The controller may also receive input from other sources, for example temperature and/or flow velocity sensors 11 and 12 through connector 13 and heater plate temperature sensor 14. In response to the user set humidity or temperature value input via dial 10 and the other inputs, controller 9 determines when (or to what level) to energise heater plate 7 to heat the water 6 within humidification chamber 5. As the volume of water 6 within humidification chamber 5 is heated, water vapour begins to fill the volume of the chamber above the water's surface and is passed out of the humidification chamber 5 outlet 4 with the flow of gases (for example air) provided from a gases supply means or blower 15 which enters the chamber through inlet 16. Exhaled gases from the patient's mouth are passed directly to ambient surroundings.

Blower 15 is provided with variable pressure regulating means or variable speed fan 21, which draws air or other gases through blower inlet 17. The speed of variable speed fan 21 is controlled by electronic controller 18 (or alternatively the function of controller 18 could be carried out by controller 9) in response to inputs from controller 9 and a user set predetermined required value (preset value) of pressure or fan speed via dial 19.

Figure 2:
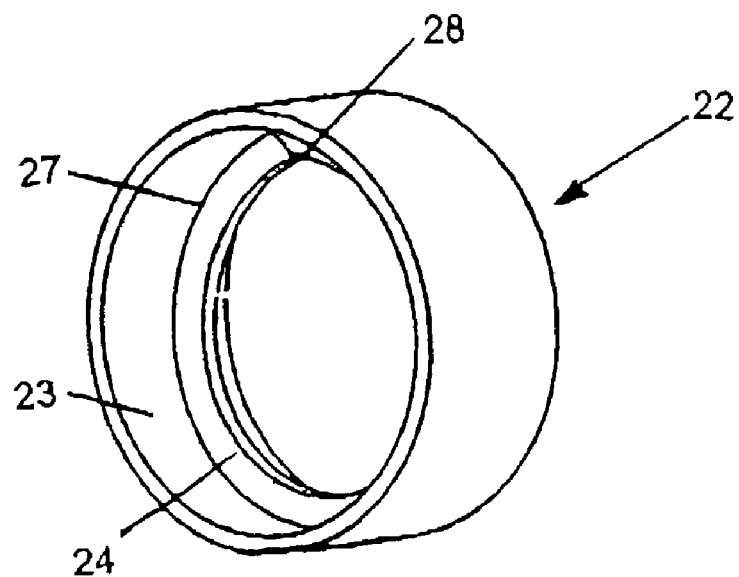
FIG. 2 is an isometric view of the sleeve used in the method of forming a conduit of the present invention.
Figure 3:
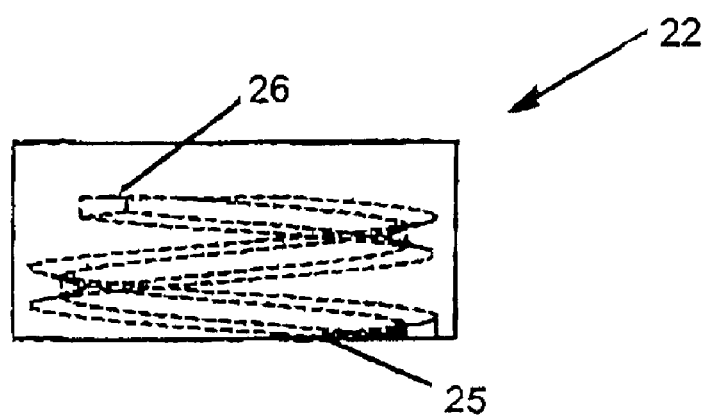
FIG. 3 is a side view of the sleeve, in particular, showing hidden detail of the thread located on the inner surface of the sleeve.

Referring now to FIGS. 2 and 3, a sleeve 22 having an internal surface 23 that is adapted for receiving a flexible conduit (indicated as 3 in FIG. 1) is shown. The conduit is preferably a double-walled helically wound flexible conduit or tube as disclosed in U.S. Pat. No. 5,848,223, but may be of other appropriate conduit construction. The internal surface 23 of the sleeve 22 has a thread 24 formed in it when moulded. The thread 24 is a complimentary size and shape to that of the outer surface of the conduit 3.

The sleeve 22 is preferably moulded from a thermoplastic material similar to the material the connector is manufactured or moulded from, but it is appreciated that other similar plastics materials may be used to construct the sleeve. The sleeve thread 24 is a helical thread having two different pitches 27 and 28. The thread 24 is shown in FIG. 2 as hidden detail. The start 25 of the thread 24 begins at the bottom of the sleeve 22 and ends 26 approximately two thirds up the height of the sleeve. The thread 24 consists of one and three-quarter rotations and has an inclining pitch 27 for one and a half rotations. The last quarter rotation 28 of the thread has no incline or decline. The ends of the thread 24 are also formed so as to taper into the inner surface of the sleeve 22; this makes it easier for a user to thread the sleeve onto the conduit.

Figure 4:
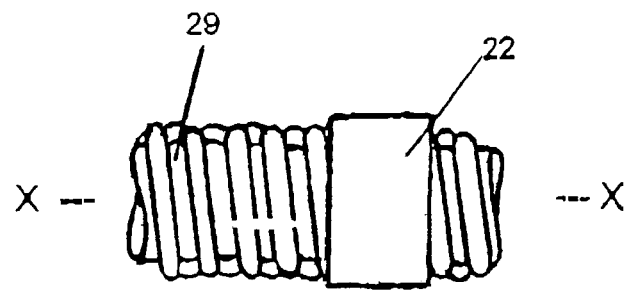
FIG. 4 is a side view of the sleeve when located about the end of a conduit.
Figure 5:
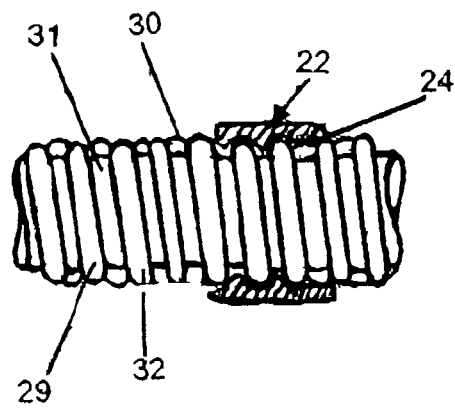
FIG. 5 is a cross sectional view of FIG. 4 taken across lines X—X.

Reference is now made to FIGS. 4 and 5, which illustrate the sleeve 22 in use and located about a flexible conduit 29. The conduit in this embodiment has an outer wall 30 and an inner wall 31 with electrical conductors (not shown) being disposed around the inner wall 31 with a support bead 32 surrounding the conductors and maintaining adhesion of the conductors to the inner wall. The support bead 32 has been heat bonded to the outside of the inner wall, this inner wall being a thin-walled tubular body. The outer wall is a ribbon applied over the wraps of the support bead spanning from one wrap to the next so as to define an outer wall for the conduit. The outer surface of the thread 24 abuts the outer wall 30 and, in the preferred form, causes a slight compression of the outer wall. As the thread 24 is slightly smaller in dimension than that of the outer wall 30 of the conduit 29, this causes there to be a tight fitting of the sleeve 22 about the conduit 29.

Figure 6:
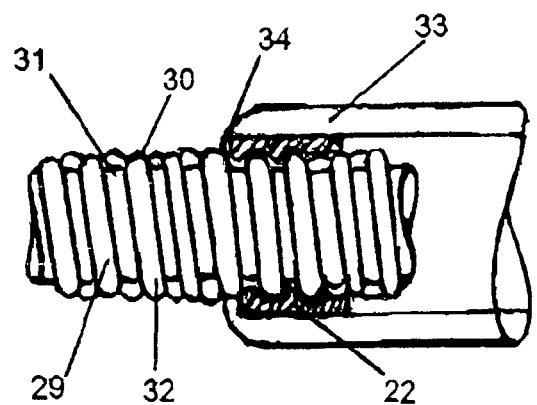
FIG. 6 is a partial cross sectional of the conduit and connector, once a connector has been moulded about the sleeve and conduit.

To obtain a conduit with a connector at one end, so that the conduit may be connected to other apparatus, such as a humidifier or blower, and to allow for gases to access and flow through said conduit, the sleeve 22 is threaded onto one end of the conduit 29. A connector is then moulded over the conduit and sleeve as shown in FIG. 6. During the over moulding process molten thermoplastic material is injected into the cavity between the sleeve 22 and the conduit 29, resulting in a seal being made between the sleeve 22 and conduit 29, so that a connector 33 is formed over the end of the conduit 29. As can be seen in FIG. 6, the sleeve 22 becomes part of the inner surface of the connector 29 as it blends with the connector 29 during moulding. Furthermore, the sleeve 22 acts as a means to determine where to locate the connector 33 on the end of the conduit 29.

Although not shown in the Figures, in other forms of the method of conduit forming of the present invention the sleeve 22 may not be fully enclosed within the connector 33, but may extend slightly out of the end 34 of the connector 33. In this form the sleeve 22 provides enhanced effect in reducing the occurrence of plastic flashings across the conduit walls.

The moulding of the connector 33 over the sleeve 22 and conduit 29 results in a seal between the conduit 29 and the connector 33 that prevents leakages in the conduit. The sleeve 22 acts to isolate the outer film layer 30 of the conduit 29 during over moulding. Furthermore, the threads spiral protrusions act as a stop to prevent molten plastic from flowing between the inner and outer walls 31, 30. In use, the sealing of the connector 33 to the conduit also prevents moisture from moving between the inner and outer walls 31, 30.

The sleeve also acts as an insulator and prevents hot molten plastic from being in contact with the conduit during over moulding, preventing damage to the conduit.

The sleeve and method of attaching a connector to a conduit of the present invention has the advantage that it prevents the connector from loosening or breaking when the conduit is bent, pulled or stressed, which can occur in some cases where the connector is attached to the conduit using a bond, such as glue. Furthermore, the occurrences of flashing of plastic across the conduit walls will be prevented during moulding, ensuring that no air or water leakages occur within the conduit walls.

Finally, the pitch of the thread on the sleeve is less than that provided by the outer wall and bead on the conduit, providing ease of assembly.

We claim:

1. A method of forming a connector on the one end of a lenght of flexible conduit, using an intermediary sleeve to protect said conduit, said sleeve comprising a section of hollow cylinder and having a thread on its interior surface of corresponding size and shape to the outer surface of said conduit, so that said cylinder can be threaded onto said at least one free end,
   wherein said method comprises the steps of:
   a) threading said sleeve onto said at least one free end, and
   b) moulding said connector over said conduit and said sleeve, said moulding causing said sleeve to become an integral part of the inner surface of said connector.

2. A method of forming a connector on the end of a flexible conduit according to claim 1 wherein said conduit is a helically wound tube having an outer wall, an inner wall, and which includes at least one electrical conductor wrapped around said inner wall which is covered with a bead.

3. A method of forming a connector on the end of a flexible conduit according to claim 1 wherein said connector is moulded over said conduit and said sleeve in such a manner that the inner part of said sleeve extends from said connector.

* * * * *

UNITED STATES PATENT AND TRADEMARK OFFICE
CERTIFICATE OF CORRECTION

| | | |
|---|---|---|
| PATENT NO. | : 7,157,035 B2 | Page 1 of 1 |
| APPLICATION NO. | : 10/314812 | |
| DATED | : January 2, 2007 | |
| INVENTOR(S) | : Deshitha Airawana Edirisuriya | |

It is certified that error appears in the above-identified patent and that said Letters Patent is hereby corrected as shown below:

Column 5, Line 2 "a connector on the one end" should be -- a connector on one end --

Column 5, Line 3 "lenght" should be -- length --

Signed and Sealed this

Second Day of October, 2007

JON W. DUDAS
*Director of the United States Patent and Trademark Office*